(12) United States Patent
Boguslavsky et al.

(10) Patent No.: US 11,861,339 B2
(45) Date of Patent: Jan. 2, 2024

(54) SYSTEMS AND METHODS FOR DEPLOYING SOFTWARE APPLICATIONS USING APPLICATION CATALOGS

(71) Applicant: Change Healthcare Holdings, LLC, Nashville, TN (US)

(72) Inventors: Rostislav Boguslavsky, Delta (CA); Diana Chaytor, Vancouver (CA); Abraham Chan, Richmond (CA); Andy YongHyuk Chung, Coquitlam (CA); Ravi Malleboina, Scarborough (CA); Stephen Ying-Kei Cheok, Port Coquitlam (CA)

(73) Assignee: Change Healthcare Holdings, LLC, Nashville, TN (US)

( * ) Notice: Subject to any disclaimer, the term of this patent is extended or adjusted under 35 U.S.C. 154(b) by 104 days.

(21) Appl. No.: 17/476,691

(22) Filed: Sep. 16, 2021

(65) Prior Publication Data

US 2023/0081153 A1  Mar. 16, 2023

(51) Int. Cl.
  *G06F 11/34* (2006.01)
  *G06F 8/61* (2018.01)
  *G16H 40/40* (2018.01)

(52) U.S. Cl.
  CPC ............ *G06F 8/61* (2013.01); *G06F 11/3476* (2013.01); *G16H 40/40* (2018.01)

(58) Field of Classification Search
  None
  See application file for complete search history.

(56) References Cited

U.S. PATENT DOCUMENTS

| | | | |
|---|---|---|---|
| 9,696,984 B2* | 7/2017 | Zhu | G06F 8/65 |
| 10,318,265 B1* | 6/2019 | To | H04L 67/34 |
| 11,245,592 B1* | 2/2022 | Thomson | G06F 9/44505 |
| 11,429,353 B1* | 8/2022 | Liguori | G06F 8/311 |

(Continued)

OTHER PUBLICATIONS

Nussbaum Lucas, "Debian Packaging Tutorial" pp. 6-45, Dec. 22, 2015.

(Continued)

*Primary Examiner* — Marina Lee
(74) *Attorney, Agent, or Firm* — Meunier Carlin & Curfman LLC

(57) ABSTRACT

In order to automate some aspects of software development, an application catalogue is provided. The application catalog is associated with an application (e.g., a medical device) and includes a plurality of parameters that each define a desired state of the software application when the software application is deployed). These parameters may include service parameters, application parameters, environmental parameters, feature parameters, API parameters, and infrastructure parameters. Before a software application is deployed to an environment, the states of the parameters with respect to the environment are determined and compared to the states of the parameters of the application catalog. The system then automatically takes the necessary steps to correct the states of any parameters of the environment to match those of application catalog. These steps may include installing services, enabling features, configuring infrastructure or environmental parameters, and allocating processing or storage resources to a virtual machine.

7 Claims, 5 Drawing Sheets

(56) References Cited

U.S. PATENT DOCUMENTS

| | | | | |
|---|---|---|---|---|
| 2012/0005342 | A1* | 1/2012 | Deng | G06Q 10/0631 |
| | | | | 709/225 |
| 2015/0378702 | A1* | 12/2015 | Govindaraju | G06F 8/60 |
| | | | | 717/177 |
| 2019/0340108 | A1* | 11/2019 | Yabusaki | G06F 11/3692 |
| 2020/0117442 | A1* | 4/2020 | Robertson | G06F 11/2033 |

OTHER PUBLICATIONS

Silva Gustavo Noronha, "APT HOWTO, Chapter 3—Managing Packages," pp. 1-9, Dec. 27, 2008.
Aaron Isotton, "Debian Repository HOWTO," pages 1-7, Dec. 26, 2008.
Wikipedia, "Package Manager," pp. 1-7, Feb. 27, 2017.
Search Report from GB2207455.3 dated Dec. 12, 2022.

* cited by examiner

SYSTEMS AND METHODS FOR DEPLOYING SOFTWARE APPLICATIONS USING APPLICATION CATALOGS

BACKGROUND

Building software applications is an arduous process that requires many manual steps. This is especially true when building software applications that are medical devices that have additional steps due to regulatory requirements. For example, building a software application typically requires steps such as installing and configuring testing hardware, building or coding the software, installing the software, configuring the software, and testing the software.

As the development and execution of software applications are moved from a local environment to a cloud-based environment, there is an increasing need to automate as much of the software development process as possible.

SUMMARY

In order to automate some aspects of software development, an application catalogue is provided. The application catalog is associated with an application and includes a plurality of parameters that each define a desired state of the software application when the software application is deployed. The software application may be a medical device. These parameters may include service parameters, application parameters, environmental parameters, feature parameters, API parameters, and infrastructure parameters. Before a software application is deployed for use, the states of the parameters with respect to an environment of the medical device are determined and compared to the states of the parameters of the application catalog. The system then automatically takes the necessary steps to correct the states of any parameters of the environment to match those of the application catalog. These steps may include installing or upgrading services, enabling or disabling one or more features, configuring one or more infrastructure or environmental parameters, and allocating processing or storage resources to a virtual machine.

In an embodiment, a method is provided. The method includes: receiving an indication to create a software application by computing system; in response to the indication, creating an application catalog by the computing system; receiving a plurality of parameters for the application catalog by the computing system, wherein the plurality of parameters relate to the deployment of the software application in an environment; receiving a request to deploy the software application in the environment by the computing system; and deploying the software application in the environment according to the application parameters by the computing system.

Embodiments many include some or all of the following features. Each of the plurality of parameters may include a state and deploying the software application in the environment according to the application parameters may include: performing operations to ensure that the states of each parameter of a plurality of parameters of the environment matches the states of each parameter of the plurality of parameters of the application catalog; and deploying the software application in the environment. The method may further include recording the performed operations to an audit log. The operations may include one or more of updating a service, installing a service; updating one or more more permissions, configuring a virtual machine, and updating the environment. The software application may be a medical device. Deploying the software application in the environment may include deploying the software application on a cloud-computing environment. The parameters may include one or more of service parameters, application parameters, environmental parameters, feature parameters, API parameters, and infrastructure parameters.

In an embodiment, a method is provided. The method includes: receiving a selection of a software application to deploy in an environment by a computing system; in response to the selection, retrieving an application catalog associated with the software application by the computing system, wherein the application catalog comprises a plurality of parameters; automatically configuring a plurality of parameters associated with the environment to match the plurality of parameters associated with the application catalog by the computing system; determining that the configuring was successful by the computing system; and in response to the determination, deploying the software application in the environment.

Embodiments may include some or all of the following features. The method may further include: determining that the configuring was not successful by the computing system; and in response to the determination, generating an error by the computing system. The application may be a medical device. Automatically configuring a plurality of parameters associated with the environment to match the plurality of parameters associated with the application catalog may include performing operations to ensure that states of each parameter of the plurality of parameters of the environment matches states of each parameter of the plurality of parameters of the application catalog. The method may further include recording the performed operations to an audit log. The operations may include one or more of updating a service, installing a service; updating one or more permissions, configuring a virtual machine, and updating the environment. Deploying the software application in the environment may include deploying the software application on a cloud-computing environment. The parameters may include one or more of service parameters, application parameters, environmental parameters, feature parameters, API parameters, and infrastructure parameters.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying figures, which are incorporated herein and form part of the specification, illustrate an application catalog system and method. Together with the description, the figures further serve to explain the principles of the application catalog system and method described herein and thereby enable a person skilled in the pertinent art to make and use the application catalog system and method.

DETAILED DESCRIPTION

Figure 1:
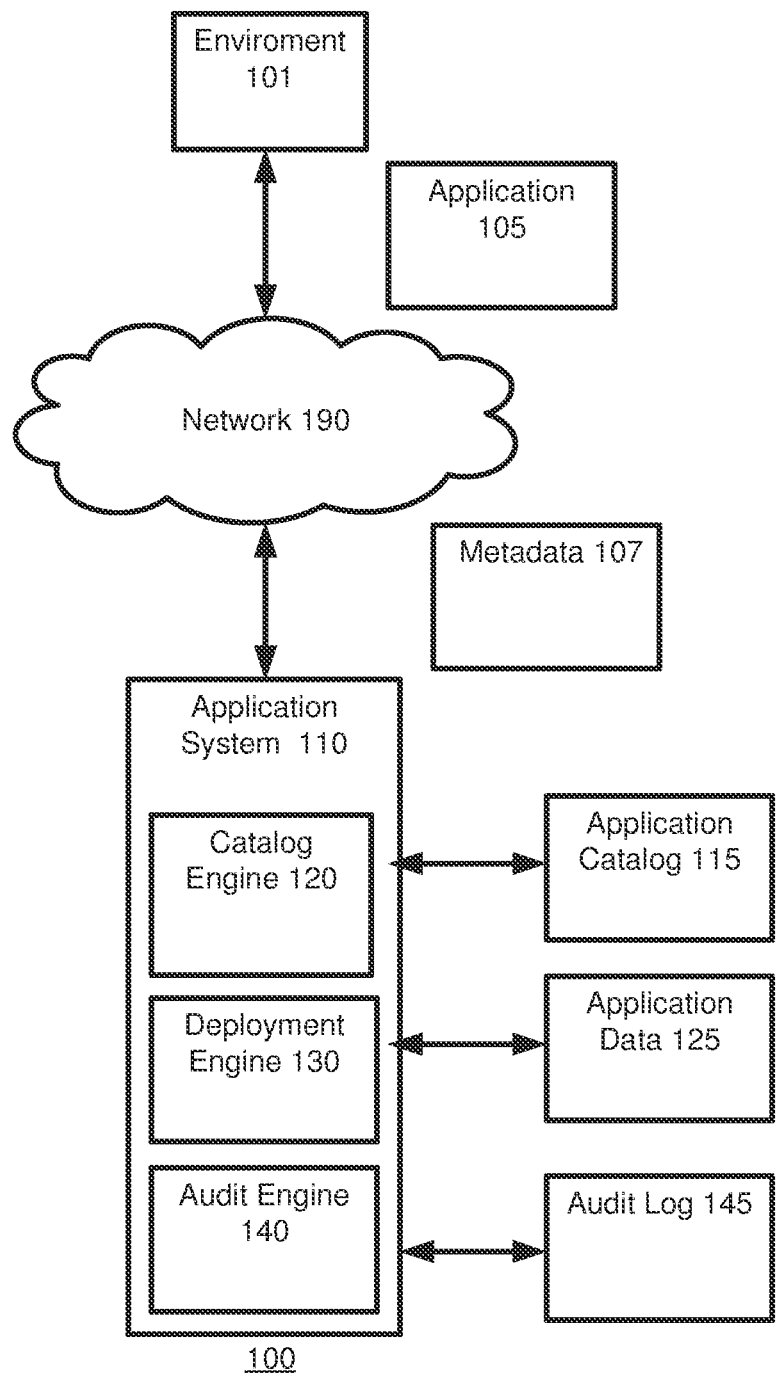
FIG. 1 is an example environment for deploying software applications to environments using application catalogs.

FIG. 1 is an example setting 100 for deploying software applications using application catalogs. The software applications may be medical devices. As shown, the setting 100 includes an application system 110 in communication with an environment 101 through a network 190. The network 190 may include a combination of private and public networks (e.g., the internet).

The software application 105 may be a medical device and may be configured to operate within an environment 101. The software applications 105 may be developed and deployed to the environment 101 by the application system 110. Depending on the embodiment, the environment 101 may be implemented in part using one or more general purpose computing devices such as the computing device 500 illustrated with respect to FIG. 5. In addition, some aspects of the environment 101 may be implemented using a cloud-based computing environment. The software application 105 may be associated with metadata 107. The metadata 107 may describe the various properties and features of the medical device implemented by the software application 105.

The application system 110 includes several components including a catalog engine 120, a deployment engine 130, and an audit engine 140. More or fewer components may be included. Each component is described further below.

The catalog engine 120 may create and maintain what is referred to as an application catalog 115 for each application 105. An application catalog is a collection of files or parameters that define desired states for the application 105 when deployed to the environment 101. Examples of states include available resources (e.g., computational and storage resources), access to particular APIs or webservices, software or service version numbers, and permission settings.

Figure 2:
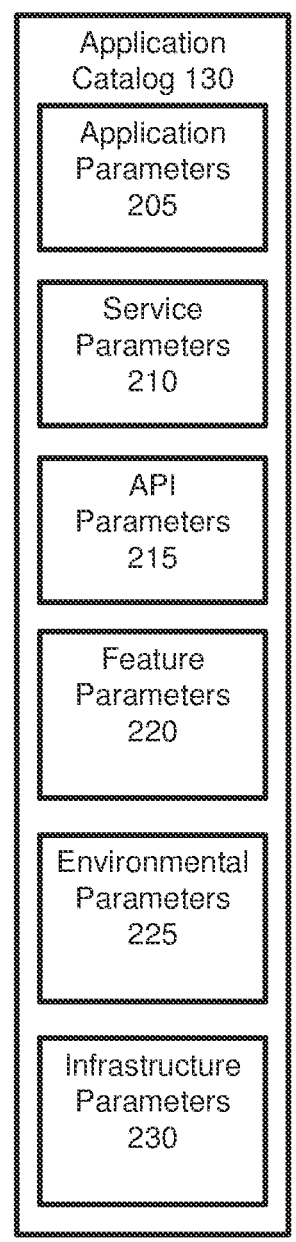
FIG. 2 is an illustration of example application catalog.

Referring to FIG. 2 is an example application catalog 115 that may be created and maintained by the catalog engine 120 for an application 105. As shown the application catalog 115 includes several parameters including application parameters 205, service parameters 210, API parameters 215, environmental parameters 225, and infrastructure parameters 230. More or fewer parameters may be supported. Depending on the embodiment, each set of parameters may be stored as a separate data structure or file. A suitable file is a YAML file. Other types of files may be supported.

The application parameters 205 may include identifiers of the application 105 (or applications 105) managed by the application system 110. The application parameters 205 may include unique identifiers of each application 105 along with a reference to a record that describes the application 105. Depending on the embodiment, the application parameters 205 may also include identifiers of the services that comprise the application 105 and version numbers associated with the services.

The service parameters 210 may include parameters about each service used by the application 105 and identified in the application parameters 205. Example service parameters 210 for a service may include, but are not limited to, a unique identifier of the service, an ingress path (e.g., URL) associated with the service, any interfaces or API paths used by the service, other servicers that the service may depend on or invoke, the network or network layer in which the service is deployed, any variables (e.g., environmental variables) or other metadata associated with the service, and information about how the service should be deployed in the environment 101. Other information may be included.

The API parameters 215 may include parameters about the various interfaces and APIs (e.g., web APIs) that are used by the services of the application 105. The parameters for each API may include version numbers and a path that is used to access the resources exposed by each API.

The feature parameters 220 may include parameters related to business and functional features. The parameters may include a unique identifier for each feature, the service or services that use or are associated with the particular feature, and an indicator of whether or not the feature is enabled or disabled with respect to a particular service.

The environmental parameters 225 may include parameters related to the environment 101 that the application 105 will be deployed into. The environmental parameters 225 may include parameters such as the name of the cloud environment 101 that will execute the application 105, indications of naming schemes and regional configurations for the environment 101, and identifiers of the applications 105 that will execute in the environment 101. Note that in some embodiments, the application 105 may be deployed to multiple environments 101, and each environment 101 may be associated with its own environmental parameters 225.

The infrastructure parameters 230 may include parameters related to the infrastructure needed to deploy the application 105 in the environment 101. These parameters may include definitions and names of storage configurations, definitions of databases, virtual machines, Kubernetes clusters, message queues, and other related information. The infrastructure parameters 230 may further include operating systems used by the application 105, IP address ranges, and other information that may be used to configure the infrastructure for the environment.

Returning to FIG. 1, a user or administrator may use the catalog engine 120 to specify the states for each of the parameters of the application catalog 115 to use when deploying the application 105. In some embodiments, the catalog engine 120 may further allow the user or administrator to add new services, features, and APIs to the application 105. When adding a new service, initially the service may be restricted to operating in a non-production domain (e.g., a domain not associated with a production application 105). The catalog engine 120 may track the testing of the service and whether or not the service has passed quality control and/or has been approved for deployment to an environment 101. The catalog engine 120 may similarly track the testing and approval for added APIs and features. Information about the newly added services, APIs, and features may be stored by the catalog engine 120 as the application data 125.

The catalog engine 120 may further allow the user or administer to update or change the states of any of the parameters associated with the application catalog 115. A record of all of the changes to the application catalog 115 may be recorded by the catalog engine 120 with the application data 125.

The deployment engine 130 may deploy the application 105 to the environment 101. In particular, the deployment engine 130, before deploying the application 105 to the environment 101, may perform one or more operations to ensure that the states of all of the parameters of the application catalog 115 (e.g., the application parameters 205, the service parameters 210, the API parameters 215, the feature parameters 220, the environmental parameters 225, and the infrastructure parameters 230) are reflected in the environment 101 (e.g., the cloud computing environment that will execute the application 105).

In some embodiments, the deployment engine 130 may deploy the application 105 using what is referred to herein as a blue green deployment. In blue green deployment, a new or updated version of the application 105 is deployed to a new environment 101 (i.e., "green") while an older version of the application 105 remains operating in an older environment 101 (i.e., "blue"). Overtime, traffic from the older version of the application 105 is gradually transferred to the new version of the application 105. After all of the traffic has been transferred, the old application 105 and environment 101 can be pulled from production and/or can standby incase the new application 105 and environment 101 needs to be pulled from production.

Depending on the embodiment, the operations performed by the deployment engine 130 may include, but are not limited to, ensuring that sufficient storage and computing resources are available to the environment 101, ensuring that the correct operating system is installed, ensuring that the correct networking resources and/or protocols are available, ensuring that the correct versions of services and APIs have been installed, and ensuring that the correct features are enabled (or disabled) for each of the services used by the application 105.

The deployment engine 130 may ensure that the states of the parameters on the device 101 match the parameters of the application catalog 115 before deploying the application 105 to the environment 101. In the event that the environment 101 has some parameters with states that cannot be updated or made equal to the states of the corresponding parameters of the application catalog 115, the deployment engine 130 may generate an error or may otherwise alert the user or administrator.

The deployment engine 130 may further record proof or evidence that the parameters of the environment 101 were verified to be in the same state as the parameters of the application catalog 115, or actions were taken to ensure that parameters of the environment 101 were verified to be in the same state as the parameters of the application catalog 115. The proof or evidence may be stored by the deployment engine 130 with the application data 125.

As may be appreciated, defining the desired parameter states in an application catalog 115, and automatically verifying that the parameters of the device 101 are in the correct states prior to deploying the application 105 in the environment 101, is an improvement over prior art systems for application deployment. Previously, before a medical device such as an application 105 could be deployed to an environment 101 such as a cloud-computing environment, an operator would typically go to the location of the environment 101 and use a printed manual to manually verify that each parameter of the environment 101 was in the correct state. For those parameters not in the correct state, the operator would have to manually configure the environment 101 to be in the correct state by, for example, manually installing or updating services, configuring network or other infrastructure settings, and activating or deactivating one or more features. Such manual installation is time consuming and error prone. Moreover, any changes made to the parameters of the application 105 by the software developers would require updating the manual or providing updated instructions to the developer, which adds further expense and time to application 105 development. Accordingly, the deployment of software applications 105 to environments 101 using an application catalog 115 is an improvement to the technical field of software development and an improvement to medical devices deployed using application catalogs 115.

The audit engine 140 may generate an audit log 145 that may be used to provide proof of compliance with one or more regulatory agencies. In some embodiments, the audit log 145 may include the history of changes that were made to the application catalog 115 during development of the application 105, various services, APIs, and features that were added to the application 105, and the testing or quality control status of each service, API, and feature. The audit log 145 may further include, for each application 105 deployment, proof that each of the parameters of the environment 101 were in the same state as the corresponding parameters in the application catalog 115.

Figure 3:
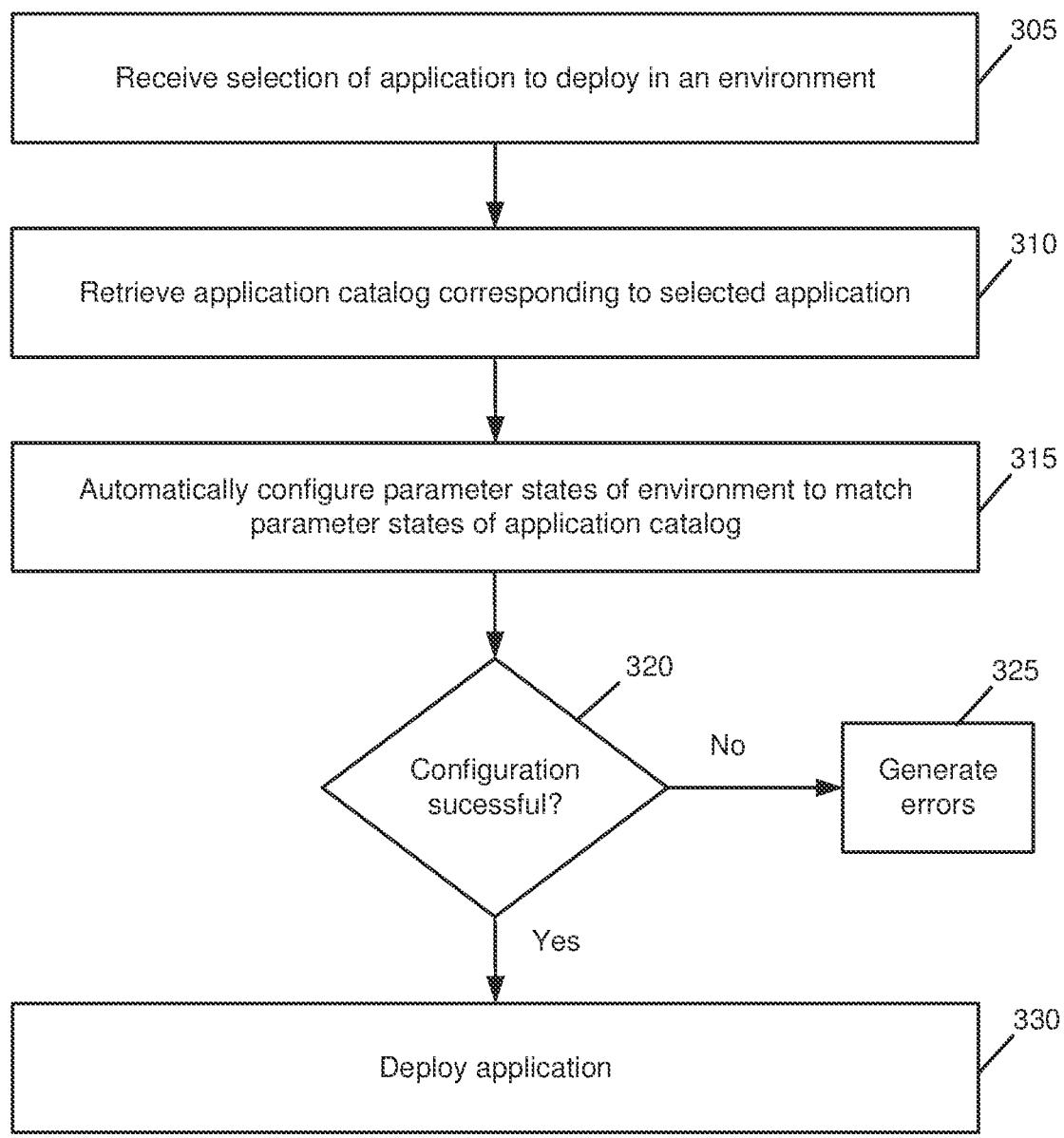
FIG. 3 is an illustration of an example method for deploying applications using an application catalog.

FIG. 3 is an illustration of an example method for deploying medical devices such as applications using an application catalog. The method 300 may be implemented by the application system 110.

At 305, a selection of an application to deploy in an environment is received. The selection of the application 105 may be received by the application system 110 from a user through the network 190. The application 105 may be a medical device. The environment 101 may be a cloud-based computing environment.

At 310, an application catalog corresponding to the selected application is retrieved. The application catalog 115 may be retrieved by the catalog engine 120. The application catalog 115 includes a plurality of parameters and each parameter is associated with a desired state. The parameters may include one or more of application parameters, service parameters, API parameters, feature parameters, environmental parameters, and infrastructure parameters. Other types of parameters may be supported.

At 315, parameter states of the environment are configured to match the states of the application catalog. The parameter states of the device 101 may be configured by the deployment engine 130. For example, the deployment engine 130 may determine the parameter states of the environment 101, compare the determined parameter states with the parameter states of the application catalog, and may identify those parameter states of the environment 101 that do not match and need to be configured. The deployment engine 130 may configure the identified parameter states by installing or upgrading one or more services of the environment 101, allocating computing resources to the environment 101, installing or upgrading a particular operating system of the environment 101, and setting one or more permissions on the environment 101.

At 320, whether the configuration was successful is determined. The determination may be made by the deployment engine 130. If the configuration was successful then the method may continue at 330. Else the method may continue at 325.

At 325, an error is generated. The error may be generated by the deployment engine 130 in response to determining that one or more parameters of the environment 101 were not successfully configured to match the state of the corresponding parameter of the application catalog 115. The error may be an electronic message and may indicate which parameters were not successfully configured.

At 330, the application is deployed to the environment. The application 105 may be deployed to the environment 101 by the deployment engine 130.

Figure 4:
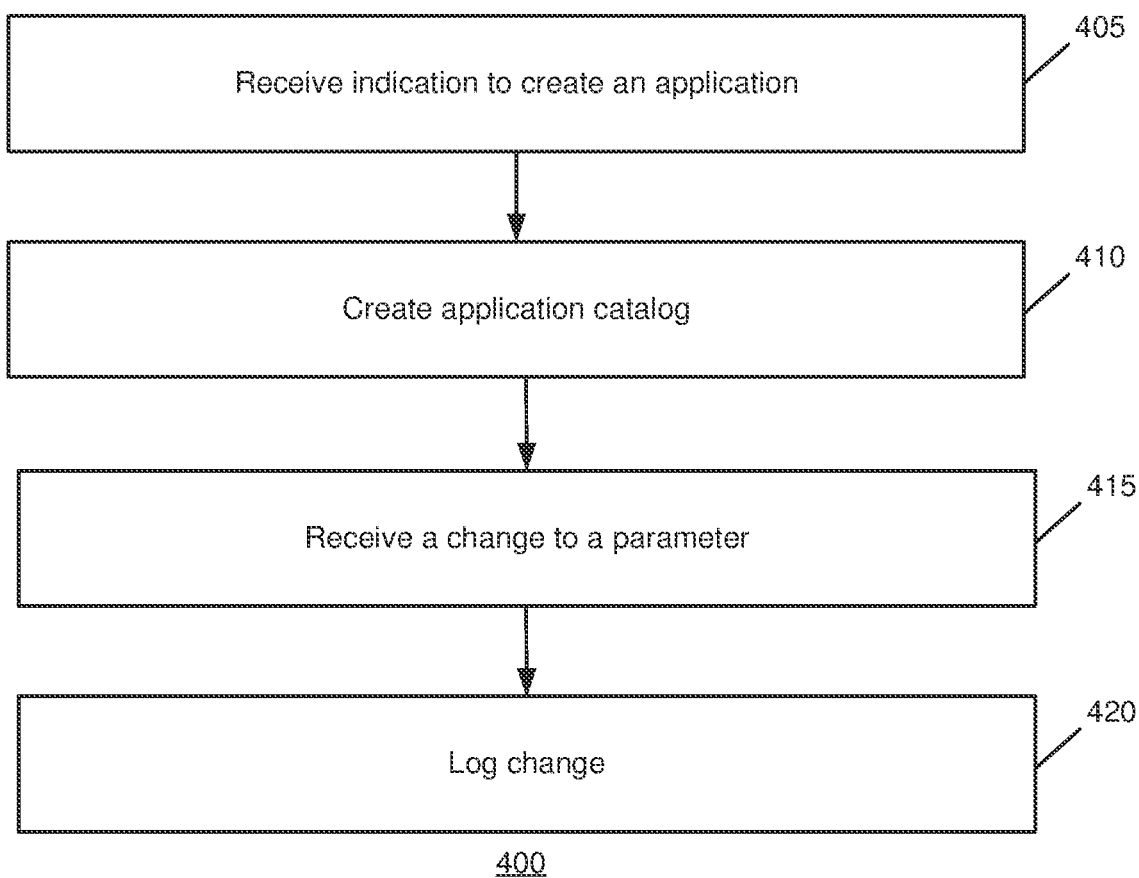
FIG. 4 is an illustration of a method for generating and using an application catalog.

FIG. 4 is an illustration of a method for generating and using an application catalog. The method 400 may be implemented by the application system 110.

At 405, an indication to create an application is received. The indication may be received by the application system 110 from a user or administrator. The application 105 may be a medical device designed to execute in an environment 101. The environment 101 may be a cloud-based computing environment.

At 410, an application catalog is created. The application catalog 115 may be created by the catalog engine 120 in response to the creating of the application 105. The application catalog 115 includes a plurality parameters that each have an associated state. The states may be desired states for the environment 101 when the application 105 is deployed to the environment 101. The states may be set by the user or administrator or may be default states that are set automatically when the application catalog 115 is created.

At 415, a change to a parameter is received. The change may be received by the catalog engine 120 from the user or administrator. For example, the user or administrator may determine that a newer version of a particular service should be used by the application 105 or may specify that more computing resources should be allocated to a virtual machine that executes the application 105.

At 420, the change is logged. The change may be logged in an audit log 145 by audit engine 140. The audit engine 140 may log or record all changes made to the application 105 and application catalog 115 for purposes of regulatory compliance, for example.

Figure 5:
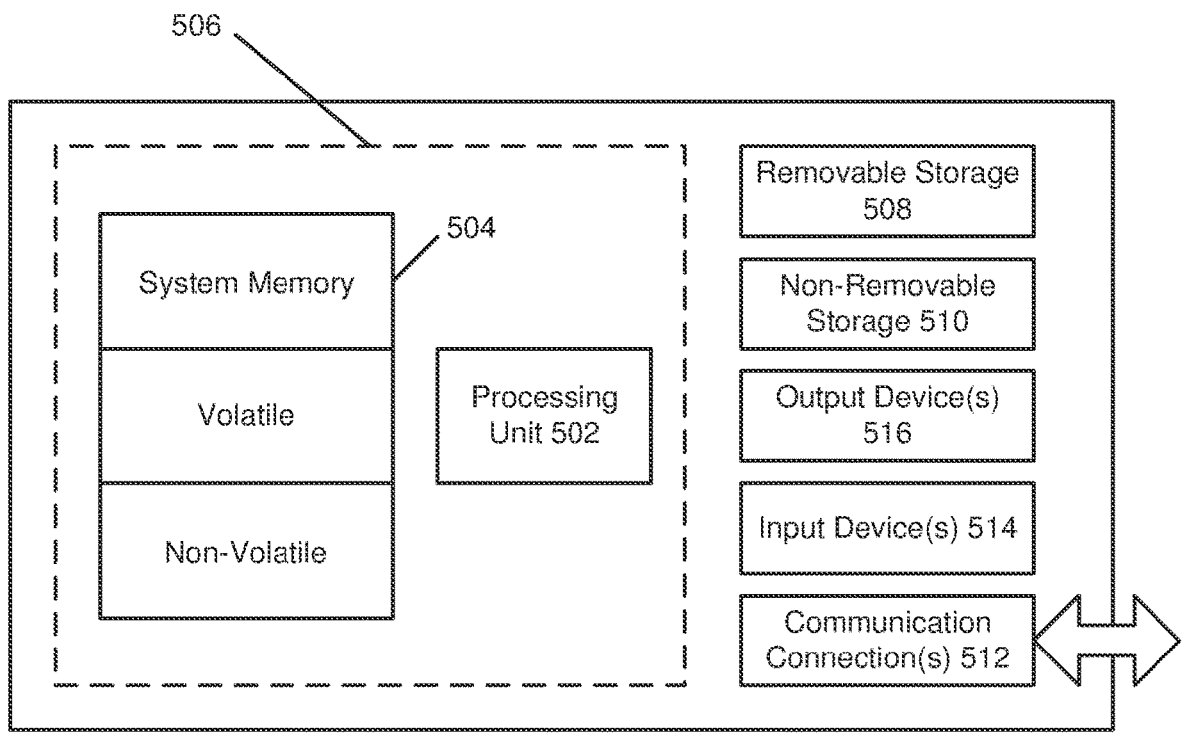
FIG. 5 shows an exemplary computing environment in which example embodiments and aspects may be implemented.

FIG. 5 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 5, an exemplary system for implementing aspects described herein includes a computing device, such as computing device 500. In its most basic configuration, computing device 500 typically includes at least one processing unit 502 and memory 504. Depending on the exact configuration and type of computing device, memory 504 may be volatile (such as random access memory (RAM)), non-volatile (such as read-only memory (ROM), flash memory, etc.), or some combination of the two. This most basic configuration is illustrated in FIG. 5 by dashed line 506.

Computing device 500 may have additional features/functionality. For example, computing device 500 may include additional storage (removable and/or non-removable) including, but not limited to, magnetic or optical disks or tape. Such additional storage is illustrated in FIG. 5 by removable storage 508 and non-removable storage 510.

Computing device 500 typically includes a variety of computer readable media. Computer readable media can be any available media that can be accessed by the device 500 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 504, removable storage 508, and non-removable storage 510 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 500. Any such computer storage media may be part of computing device 500.

Computing device 500 may contain communication connection(s) 512 that allow the device to communicate with other devices. Computing device 500 may also have input device(s) 514 such as a keyboard, mouse, pen, voice input device, touch input device, etc. Output device(s) 516 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:
receiving, by one or more processors, a request to deploy a software application in an environment of a medical device;
deploying, by the one or more processors, the software application in the environment of the medical device according to a plurality of application parameters from an application catalog, wherein each of the plurality of application parameters comprises a state, and
deploying the software application in the environment according to the plurality of application parameters comprises:
performing operations to ensure that the states of each parameter of a plurality of environment parameters of the environment matches the states of each parameter of the plurality of application parameters, wherein the operations comprise at least one of updating a service, installing a service; updating one or more permissions, configuring a virtual machine, or updating the environment;
generating an audit log that comprises proof that the states of each parameter of the plurality of environment parameters of the environment matches the states of each parameter of the plurality of application parameters; and
deploying the software application in the environment of the medical device; and
providing, by the one or more processors, the audit log to one or more regulatory agencies as proof of compliance.

2. The method of claim 1,
wherein prior to receiving the request to deploy the software application in the environment of the medical device, creating, by the one or more processors, the application catalog, wherein creating the application catalog comprises:
receiving, by the one or more processors, an indication to create the software application in the medical device; and
receiving, by the one or more processors, the plurality of application parameters.

3. A method comprising
receiving, by one or more processors, a selection of a software application to deploy in an environment of a medical device;
in response to the selection, receiving, by the one or more processors, an application catalog associated with the software application, wherein the application catalog comprises a plurality of application parameters, wherein each of the plurality of application parameters comprises a state;
automatically configuring, by the one or more processors, a plurality of environmental parameters associated with the environment of the medical device to match the plurality of application parameters associated with the application catalog, wherein automatically configuring the plurality of environmental parameters associated with the medical device to match the plurality of application parameters associated with the application catalog comprises:
performing operations to ensure that states of each parameter of the plurality of environmental parameters matches the states of each parameter of the plurality of application parameters, wherein the performed operations comprise at least one of updating a service, installing a service, updating one or more permissions, configuring a virtual machine, and updating the environment; and
generating an audit log that comprises proof that the states of each parameter of the plurality of environment parameters of the environment matches the states of each parameter of the plurality of application parameters;
determining, by the one or more processors, that the configuring was successful; and
in response to the determination, deploying, by the one or more processors, the software application in the environment of the medical device and providing the audit log to one or more regulatory agencies as proof of compliance.

4. The method of claim 3, further comprising:
determining that the configuring was not successful by the computing system; and
in response to the determination, generating an error by the computing system.

5. The method of claim 3, wherein performing operations to ensure that states of each parameter of the plurality of environmental parameters matches the states of each parameter of the plurality of application parameters comprises:
determining the states of the plurality of application parameters associated with the application catalog;
determining the states of the plurality of environmental parameters associated with the environment;
determining one or more states of the plurality of environmental parameters associated with the environment that do not match corresponding one or more states of the plurality of application parameters associated with the application catalog; and
performing operations to cause the determined one or more states of the plurality of environmental parameters associated with the environment to match the corresponding one or more states of the plurality of application parameters associated with the application catalog.

6. A system comprising:
memory storing an application catalog and a software application; and
one or more processors communicatively coupled to the memory, wherein the one or more processors perform actions comprising:
receive a selection of the software application to deploy on in an environment in a medical device;
in response to the selection, receive the application catalog associated with the software application, wherein the application catalog comprises a plurality of application parameters, wherein each of the plurality of parameters comprises a state;
automatically configure a plurality of environmental parameters associated with the environment of the medical device to match the plurality of application parameters associated with the application catalog, wherein automatically configuring the plurality of environmental parameters associated with the medical device to match the plurality of application parameters associated with the application catalog comprises:

performing operations to ensure that states of each parameter of the plurality of environmental parameters matches the states of each parameter of the plurality of application parameters, wherein the performed operations comprise at least one of updating a service, installing a service, updating one or more permissions, configuring a virtual machine, and updating the environment; and generating an audit log that comprises proof that the states of each parameter of the plurality of environment parameters of the environment matches the states of each parameter of the plurality of application parameters;

determine that the configuring was successful; and in response to the determination, deploy the software application in the environment of the medical device and providing the audit log to one or more regulatory agencies as proof of compliance.

7. The system of claim 6, wherein the one or more processors perform actions further comprising:

determine that the configuring was not successful; and in response to the determination, generate an error.

* * * * *